United States Patent [19]

Webster, Jr.

[11] Patent Number: 4,576,177
[45] Date of Patent: Mar. 18, 1986

[54] CATHETER FOR REMOVING ARTERIOSCLEROTIC PLAQUE

[76] Inventor: Wilton W. Webster, Jr., 1388 Crest Dr., Altadena, Calif. 91001

[21] Appl. No.: 518,817

[22] Filed: Aug. 1, 1983

Related U.S. Application Data

[63] Continuation-in-part of Ser. No. 467,754, Feb. 18, 1983, abandoned.

[51] Int. Cl.$^4$ .............................................. A61B 10/00
[52] U.S. Cl. .................................. 128/660; 128/303.1
[58] Field of Search .............. 128/660, 661, 663, 4–8, 128/303.1, 395–398

[56] References Cited

U.S. PATENT DOCUMENTS 4,146,019  3/1979  Bass et al. ................................. 128/6
4,319,580  3/1982  Colley et al. ........................ 128/661

OTHER PUBLICATIONS

Lutz, H. et al., "Transgastroscopic Ultrasonography, *Endoscopy*, vol. 8, pp. 203–205, 1976.
Auth, D. C. et al., "A High-Power Gastric Photocoagulator for Fiberoptic Endoscopy," IEEE BME Trans., vol. BME-23, #2, pp. 129–135, Mar. 1976.
Hisanaga, K. et al., "A New Trans-Digestive-Tract Scanner with a Gastro-Fiber-Scope" Proc. 23rd Ann. Meeting AIUM, 1978.
Garrett, Lee, "A Catheter Assembly", International published PCT Application WO83/01893, publ. Jun. 9, 1983.
Martin, Roy et al., "A UTS Catheter for Inter Vascular Measurement of Blood Flow: Technical Details," IEEE Trans. on Sonics and UTS, vol. SU-27, No. 6, pp. 277–286, Nov. 1980.
Olson, R. et al., "A NDT UTS Technique to Measure Diameter and Blood Flow in Arteries", IEEE BME Trans., vol. 21, No. 2, pp. 168–171, Mar. 1974.
Duck, F. A. et al., "An Intravenous Doppler Probe for Arterial Flow Monitoring" Ultrasonics, Conf. Dig. of 3rd Intnl. Conf. on Med. Physics, Göteborg Sweden, 1972.
Grady, D. "The Artery Zapper", Discover Magazine, Dec. 1982, pp. 36–37 and 40.
Hartley, C. J. et al., "A Single-Crystal UTS Catheter-Tip Velocity Probe", Med. Instrumentation, vol. 8, No. 4, Jul.–Aug. 1974.
Hetzel, M. R. et al., "Laser Treatment for Carcinoma of the Bronchus," Brit. Med. Jrnl., Jan. 1, 1983.
Hartley, C. J. et al., "A Pulsed Doppler Catheter for Measuring Coronary Artery Velocity," Conf. Proc. of the 26th Ann. Conf. on Engs. in Med. & Biol., Minneapolis, Minn., Sep. 30–Oct. 4, 1973, p. 85.

*Primary Examiner*—Kyle L. Howell
*Assistant Examiner*—Francis J. Jaworski
*Attorney, Agent, or Firm*—Christie, Parker & Hale

[57] ABSTRACT

An apparatus and method for identifying and removing arteriosclerotic plaque deposits from blood vessels is disclosed. The apparatus comprises a catheter having an optical fiber for transmitting laser irradiation and an ultrasonic transducer mounted at the tip of the catheter for transmitting and receiving ultrasonic signals. The apparatus further comprises a transmitting unit for generating electrical impulses for activating the ultrasonic transducer, a receiving unit for displaying electrical signals from the ultrasonic transducer and a laser. Arteriosclerotic plaque deposits are identified by the ultrasonic echoes which result from transmitted ultrasonic signals and are removed by laser irradiation.

27 Claims, 7 Drawing Figures

CATHETER FOR REMOVING ARTERIOSCLEROTIC PLAQUE

This invention is a continuation-in-part of U.S. patent application Ser. No. 467,754 filed Feb. 18, 1983, entitled CATHETER FOR REMOVING ARTERIOSCLEROTIC PLAQUE and now abandoned, which is incorporated herein by reference.

FIELD OF THE INVENTION

This invention relates to catheters and specifically to a catheter for identifying and removing arteriosclerotic plaque deposits in blood vessels.

BACKGROUND OF THE INVENTION

Arteriosclerotic plaque deposits which occlude and restrict the blood flow of coronary arteries are a major cause of heart disease. Treatment of such arteriosclerotic plaque has traditionally included open heart surgery or angioplasty.

Presently there is growing interest in the use of laser irradiation to remove arteriosclerotic plaque from occluded blood vessels, particularly coronary arteries. Such laser irradiation is delivered to the occluded vessel by means of a catheter comprising an optical fiber. Laser light is passed through the optical fiber and onto the arteriosclerotic plaque. A laser beam, thus delivered, has been found to remove arteriosclerotic plaque resulting in patency of the blood vessel.

For example, *Circulation*, Volume 66, Supplement II (October, 1982) at page 368 describes a method wherein a fiberscope including quartz fiber was inserted via the left subclavian artery to the aortailiac bifurcation in a dog. The right iliac artery was then successfully photoirradiated by YAG laser.

*Circulation*, Volumne 66, Supplement II (October, 1982) at page 366 describes a method using laser irradiation, delivered through a silicon fiber to the right iliac artery of rabbits to remove arteriosclerotic plaque.

The use of laser irradiation to remove arteriosclerotic plaque requires means to accurately position the end of the optical fiber with respect to the plaque which is to be removed. It also requires means to determine the thickness and hardness of the arteriosclerotic plaque deposit so that plaque removal may be maximized while arterial damage is minimized.

Methods for positioning the end of the optical fiber include X-ray fluoroscopy and/or viewing through a flexible fiberoptic scope inserted into the occluded artery. For example, U.S. Pat. No. 4,207,874 to Choy describes a device using X-ray fluoroscopy and viewing through a fiberoptic scope to locate obstructions in blood vessels and the like. Laser irradiation is then transmitted through an optical fiber to vaporize the obstruction.

X-ray fluoroscopy methods involve the positioning of the catheter tip by the injecton of a radiopaque material into the occluded blood vessel and viewing the X-ray shadow images of the artery and the catheter by a fluoroscope. Such images do not generally give sufficient detail of the occluded blood vessel to accurately and safely position the catheter tip with respect to an arteriosclerotic plaque deposit. Further, X-ray fluoroscopy methods also provide little information regarding thickness and density of the plaque deposits.

Fiberoptic scopes have both illumination and viewing capabilities but require blocking of the blood flow through the blood vessel followed by flushing of the blood vessel with a clear liquid such as saline, until a clear pathway is achieved. Viewing can then be done with the eye directly or, for example, with a television camera and monitoring system.

There are several disadvantages associated with the fiberoptic scope methods, including the fact that viewing cannot be done during laser irradiation and that the blood flow must be stopped during viewing. Further, viewing by a fiberoptic scope reveals little or no information with regard to the thickness or density of the arteriosclerotic plaque deposit. Also, fiberoptic scopes tend to be very expensive and generally have only a limited life before costly repairs are required.

SUMMARY OF THE INVENTION

In accordance with the present invention, there is provided an apparatus for determining the position and character of occlusions in blood vessels, such as arteriosclerotic plaque, and for removing occlusions whose position and character have been determined. The apparatus comprises a catheter, a transmitting unit, a receiving unit and a laser.

The catheter comprises a catheter tube with an ultrasonic transducer mounted at the distal tip of the catheter tube. An optical fiber is disposed within the catheter tube and extends the length of the catheter tube. The ultrasonic transducer is electrically connected to the transmitting unit and the receiving unit by a pair of wires which are also disposed in and extend the length of the catheter tube.

The catheter is inserted into and positioned within a blood vessel. The ultrasonic transducer is activated by an electrical impulse generated by the transmitting unit and delivered through the wires. The ultrasonic transducer transmits an ultrasonic signal in response to the electrical impulse. The ultrasonic transducer then receives ultrasonic echoes, i.e., ultrasonic signals reflected by the tissues surrounding the catheter tip, and transmits electrical signals to the receiving unit in response to the received ultrasonic echoes. The received electrical signals carry information regarding the distance and character of the tissues which reflect the ultrasonic signals and constitutes a "signature" of the tissues. The presence of occlusions can be determined from the signature.

Occlusions whose position and character have been determined can be removed by laser irradiation which is directed from the laser through the optical fiber onto the occlusion.

In a preferred embodiment of the invention, the transmitting unit has two modes. The first mode is a pulse-echo mode wherein a short electrical impulse is generated and delivered to the ultrasonic transducer which transmits an ultrasonic pulse signal in response. Ultrasonic echoes are then received by the ultrasonic transducer which generates electrical signals which are delivered to the receiving unit. These electrical signals provide a signature of the surrounding tissue.

The second mode is a pulsed-doppler mode wherein the transmitting unit generates electrical bursts which are delivered to the ultrasonic transducer which transmits tone bursts in response. Ultrasonic echoes from the tone bursts are received by the ultrasonic transducer which generates electrical signals which are delivered to the receiving unit and are used to determine the blood flow velocity at two selected distances from the catheter tip. The tissue signature and the change in blood flow velocity are used to determine the presence of occlusions.

In a particularly preferred embodiment of the invention, the ultrasonic transducer is mounted at an angle from the longitudinal axis of the catheter so that the transmitted ultrasonic signal is generally directed toward the blood vessel wall. The catheter also comprises coupling optics to direct laser irradiation, transmitted from the distal tip of the optical fiber, in the direction of the transmitted ultrasonic signal.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
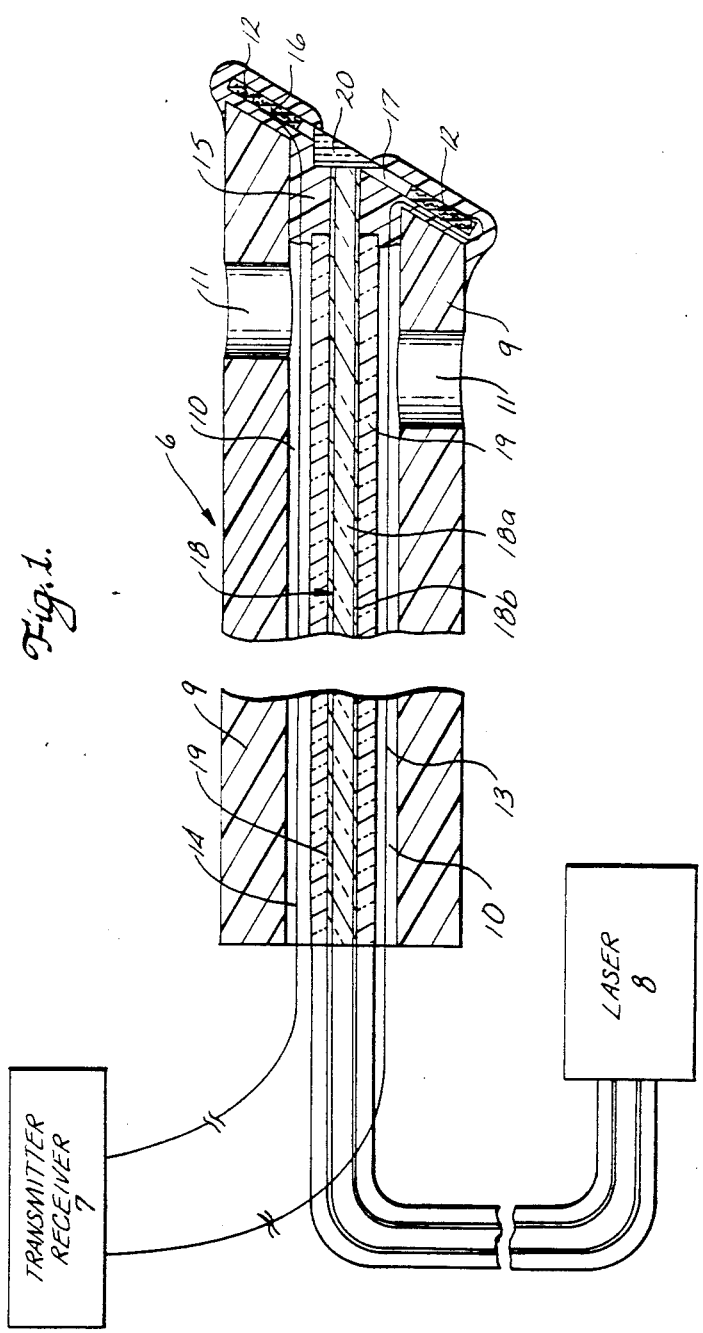
FIG. 1 is a schematic of an apparatus according to the invention including an enlarged cross-sectional view of a preferred catheter.

The present invention is particularly applicable to removing arteriosclerotic plaque deposits from blood vessels, especially coronary arteries. With reference to FIG. 1, a preferred apparatus comprises a catheter 6, a transmitter-receiver 7, and a laser 8.

The catheter 6 comprises an elongated flexible catheter tube 9 constructed out of a suitable biologically non-reactive material, e.g., polyurethane. The catheter tube 9 has a generally circular, transverse cross-section.

The preferred outer diameter of the catheter tube 9 varies according to the application, i.e., according to the size of the blood vessel within which the catheter is positioned. For example, a catheter having an outer diameter of about 1 millimeter is presently preferred for identifying and removing arteriosclerotic plaque deposits in coronary arteries.

The lumen of the catheter tube also has a generally circular transverse cross-section. The diameter of the lumen is sufficiently large to enable an optical fiber and a pair of wires to be disposed through the lumen and is preferably sufficiently large to provide a space 10 between the optical fiber and the catheter tube wall. Further, the catheter tube 9 comprises holes 11 at its distal end which extend from the space 10 through the wall of the catheter tube. The space 10 and holes 11 provide a passage for the injection of a radiopaque material through the catheter into the blood vessel which allows the rapid positioning of the distal tip of the catheter in the approximate area of the suspected plaque deposit by X-ray fluoroscopy. The same passage can also be used for the withdrawal of a sample of the blood or fluid in the blood vessel following irradiation of an arteriosclerotic plaque deposit.

An ultrasonic transducer 12 is mounted at the distal end of the catheter tube 9 and is electrically connected on opposite sides to a pair of wires 13 and 14, which extend through the lumen of the catheter tube to the transmitter-receiver 7. Ultrasonic transducers suitable for use with catheters are known in the art. For example, see *Circulation,* Volume 56, No. 1 (July, 1977) pages 18 to 25; *IEEE Transactions on Sonics and Ultrasonics,* Volume SU-27, No. 6 (November, 1980) pages 277 to 286.

The ultrasonic transducer 12 is generally disc-shaped and has a substantially flat face 16 and a generally circular opening 17 through its center. The preferred outer diameter of the ultrasonic transducer is about the same as the outer diameter of the catheter tube and likewise varies according to the application in which the catheter is used. For removing arteriosclerotic plaque from coronary arteries, a diameter of about 1 millimeter is presently preferred. The diameter of the opening 17 is generally not critical but is sufficiently large to enable the distal end of an optical fiber 18 to extend into and through the opening 17.

The thickness of the ultrasonic transducer is also not critical. For a disc-shaped ultrasonic transducer having a diameter of about 1 millimeter, a thickness of about 0.1 to about 0.3 millimeters is suitable.

The ultrasonic transducer 12 is made of a piezoelectric material, preferably a piezoelectric ceramic crystal and generally has a response frequency of from about 10 to about 30 MHz. The presently preferred piezoelectric material comprises lead zirconate-titanate.

The ultrasonic transducer 12 is mounted at the distal end of the catheter tube 9 so that the plane of the front face of the ultrasonic transducer is at selected angle to the longitudinal axis of the catheter tube. In this arrangement, the ultrasonic signals transmitted from the transducer are directed toward the wall of the blood vessel rather than along the length of the blood vessel. In other words, the included angle between the plane of the face of the ultrasonic transducer and the longtitudinal axis of the catheter body is less than 90°.

The ultrasonic transducer 12 may be attached to the distal end of the catheter tube 11 by any suitable means, such as by epoxy cement 15.

The distal ends of wires 13 and 14 are electrically connected to opposite sides of the ultrasonic transducer 12, by conventional means such as soldering, ultrasonic bonding, cold welding and the like. Wires 13 and 14 can be made of any suitable metal, such as copper, stainless steel, or the like. The wires are preferably clad with a non-conductive coating, e.g., nylon, to assure that electrical contact between the wires is prevented.

An optical fiber 18 is disposed within the lumen of the catheter tube 9. The optical fiber has a generally circular transverse cross-section and comprises a core 18a made of fused silica or its equivalent surrounded by an optical clad 18b made of a material having a lower refractive index than the core, as is well known in the art. Surrounding the optical fiber 18 is a protective buffer 19 which is generally made of a semi-rigid plastic such as an epoxy resin or the like.

The optical fiber 18 has a diameter sufficiently large to transmit laser irradiation of sufficient strength to vaporize arteriosclerotic plaque desposits without a detrimental increase in the temperature of the optical fiber. The presently preferred diameter is about the minimum diameter which results in a safe increase in temperature during laser transmission in order to minimize the overall diameter of the catheter. For removing arteriosclerotic plaque from coronary arteries, an optical fiber having a diameter in the range of from about 0.1 millimeters to about 0.5 millimeters is preferred.

At the distal end of the optical fiber 18, the protective sheath is removed or cut back and the distal tip of the optical fiber 18 is rigidly mounted within the central opening 17 of the ultrasonic transducer 12. Mounting can be done by any suitable means, such as by epoxy cement. The diameter of the central opening 17 of the ultrasonic transducer is sufficiently larger than the diameter of the optical fiber to allow the distal tip of the optical fiber to be mounted within the opening 17, and to provide a sufficient gap between the ultrasonic transducer and the optical fiber to prevent detrimental heating of the ultrasonic transducer as a result of heat generated by the optical fiber during laser transmission.

In such an arrangement, wherein the tip of the optical fiber is mounted in the opening of the transducer, laser irradiation is transmitted from the center of the ultrasonic transducer. To direct the laser irradiation in the same general direction as the transmitted ultrasonic signal, i.e., toward the wall of the blood vessel, coupling optics are used. A microlens 20 or its equivalent is mounted within the opening 17 in the transducer adjacent the distal tip of the optical fiber 18 so that laser irradiation emanating from the tip of the optical fiber will pass through the microlens 20 which changes the direction of the laser irradiation to about the center of the transmitted ultrasonic signal. Mounting of the microlens may be by any suitable means, such as epoxy cement.

The transmitting and receiving units may be of conventional design. In a preferred embodiment of the invention, the transmitting unit and receiving unit are combined in a single transmitter-receiver 7.

The transmitter-receiver comprises two modes of operation and means for switching between the two modes. The first mode is a pulse-echo mode which activates the ultrasonic transducer to transmit an ultrasonic pulse signal and senses the time delay and amplitude content of the ultrasonic echoes resulting from the transmitted ultrasonic pulse signal for identification of the tissue character at a selected distance from the catheter tip.

The second mode is a pulsed-doppler mode which activates the ultrasonic transducer to transmit a tone burst and senses the phase and frequency of echoes resulting from the transmitted tone burst for identifying the blood flow velocity at two selectable distances from the catheter tip. The pulsed-doppler mode is used to determine the presence of a restriction in the blood vessel and the pulse-echo mode is used to identify the character of the tissue causing the restriction.

In the pulse-echo mode, the transmitter-receiver generates short electrical impulses at selected intervals which are delivered to the ultrasonic transducer 12 through wires 13 and 14. The ultrasonic transducer emits an ultrasonic signal in response to each electrical impulse. Ultrasonic echoes, i.e., reflections of the transmitted ultrasonic signal, are received by the transducer which then transmits electrical signals, corresponding to the received echoes, back to the transmitter-receiver, again through wires 13 and 14. The time delay and amplitude content of the ultrasonic echoes are determined from the received electrical signals and provide a "signature" of the reflecting tissue. Analysis of this signature provides information related to the distance and character, e.g., density, of the reflecting tissue.

Figure 2:
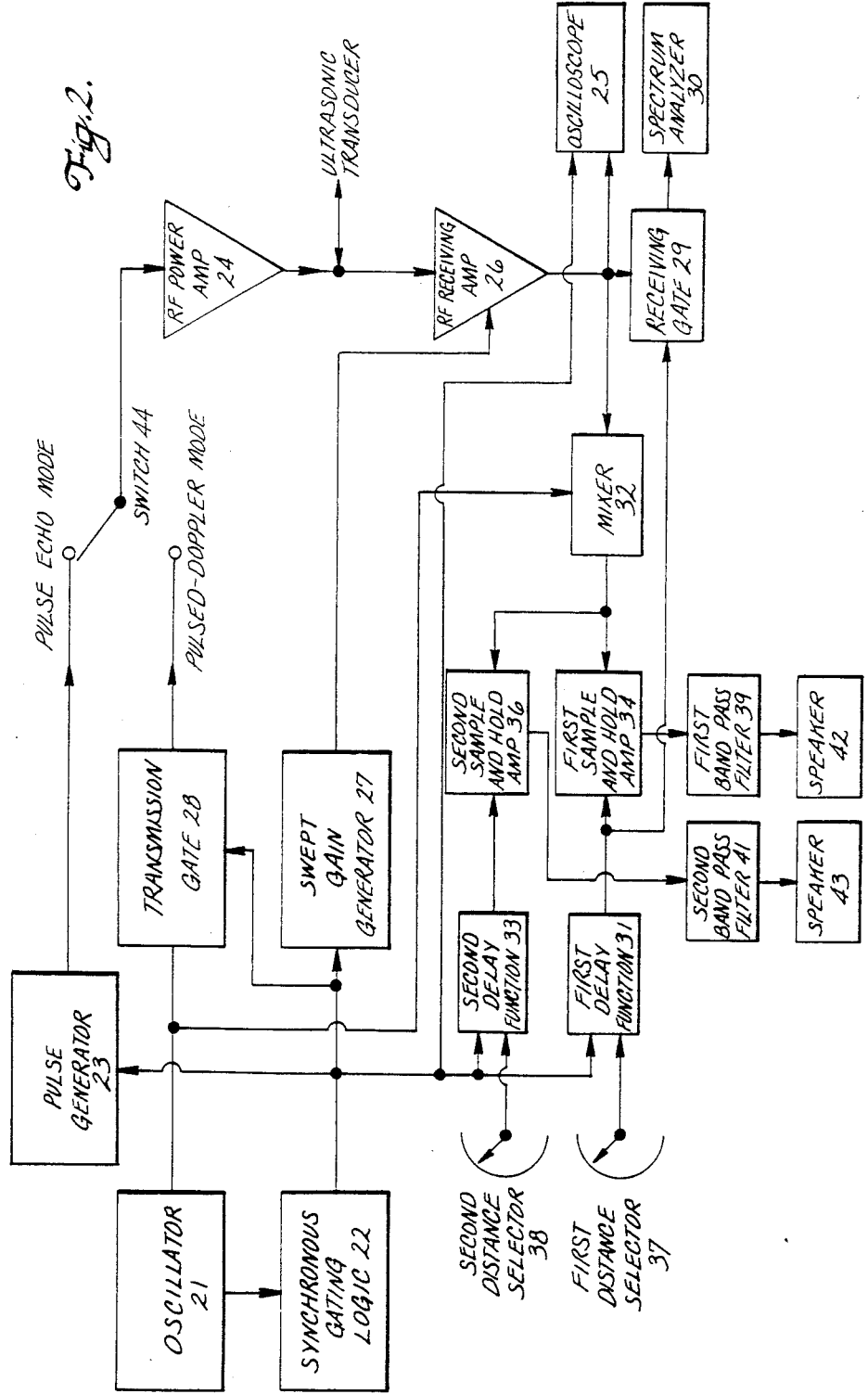
FIG. 2 is a block diagram of a transmitter-receiver applicable to this invention.

With reference to FIG. 2, the transmitter-receiver comprises an oscillator 21 which controls the timing of the pulse-echo mode. A synchronous gating logic 22 triggers a pulse generator 23 to produce a single short electrical impulse at selected intervals, e.g., intervals in the 50 to 100 KHz range, for activating the ultrasonic transducer. The electrical impulse is short, comprising as little as a single cycle of the oscillator signal.

The short electrical impulse is amplified by a radio frequency power amplifier 24 and is delivered by wires 13 and 14 to the ultrasonic transducer 12. The ultrasonic transducer emits an ultrasonic pulse signal in response to the short electrical impulse. The interval between consecutive electrical impulses is sufficient to allow the ultrasonic transducer to receive reflected ultrasonic echoes resulting from the transmitted ultrasonic pulse signal and to transmit electrical signals to the transmitter-receiver in response to those ultrasonic echoes before transmitting another ultrasonic pulse signal.

Ultrasonic echoes, i.e., reflections of the transmitted ultrasonic signal, occur at every boundary between materials differing in the velocity of the propagation of sound, including boundaries between blood and arteriosclerotic plaque deposits and between arteriosclerotic plaque deposits and the wall of the blood vessel.

The ultrasonic echoes are received by the ultrasonic transducer which transforms the ultrasonic echoes into electrical signals which are transmitted to the transmitter-receiver through wires 13 and 14. The electrical signals from the ultrasonic transducer are sensed and amplified by a radio frequency receiving amplifier 26. The gain of the radio frequency receiving amplifier 26, i.e., the increase in signal amplitude, is controlled by a swept gain generator 27 which compensates for the reduced signal amplitude of echoes returning from greater distances. The amplified signal is then displayed or monitored by any suitable means, e.g., an oscilloscope 25, and provides a "signature" of the reflecting tissue.

To display the amplified signal on the oscilloscope 25, a transmission gate 28 is used as an oscilloscope trigger for indicating the onset of the transmitted electrical pulse. Direct observation of the amplified signal received from the ultrasonic transducer on the oscilloscope 25 provides information related to the distance of the reflecting tissue, as determined by the time on the oscilloscope trace, and the character of the tissue interface as determined by the amplitude of reflection on the oscilloscope trace.

The amplified signal can also be gated by a receiving gate 29 to provide a signal which can be used by a spectrum analyzer for further identification of the character or properties of the reflecting tissue. The receiving gate 29 removes all portions of the signal except that portion corresponding to a selected distance from the catheter tip. To accomplish this, the receiving gate 29 is controlled by a first delay function 31 which activates the receiving gate 29 to pass a signal of preset width at a selected time after the transmission gate 28 has signaled the onset of the transmitted electrical impulse.

To determine the presence of arteriosclerotic plaque deposits in a blood vessel from the tissue signature, a comparison is made between the signature of the unknown tissue and previously obtained signatures for which the character of the tissue, i.e., the presence or absence of arteriosclerotic plaque, was determined by conventional means. That is, preceding the analysis of an unknown tissue, tests are performed, for example on laboratory animals, wherein the catheter is inserted into non-occluded blood vessels, i.e., blood vessels having little or no arteriosclerotic plaque, as well as blood vessels occluded to various degrees by arteriosclerotic plaque, and tissue signatures are obtained from those blood vessels. The character of the tissues, i.e., the amount of arteriosclerotic plaque, of the "test" blood vessels is then determined by visual inspection, e.g., surgery, or other conventional means and a correlation between the presence and amount of arteriosclerotic plaque and the tissue signatures is made. Once a correlation is made, the presence and amount of plaque in an unknown blood vessel can then be determined from the signature of that tissue.

In the pulsed-doppler mode, the transmitter-receiver generates electrical bursts, i.e., electrical signals comprising multiple cycles, e.g., ten to twenty cycles, of the oscillator signal which are delivered to the ultrasonic transducer and results in the transmission of a tone burst, i.e., a longer ultrasonic signal having a duration corresponding to the duration of the electrical burst. Comparison of the phase and frequency of the ultrasonic echoes resulting from a transmitted tone burst, at two or more selected times following the transmission, with a signal from the oscillator provides information which yields the velocity of the blood flow at two distances from the transducer.

Again with reference to FIG. 2, the synchronous gating logic 22 of the transmitter-receiver sends a signal to the transmission gate 28 to transmit an electrical signal comprising a select number of cycles of the oscillator signal at selected intervals, e.g., an interval in the 50–100 KHz range, the electrical signal is amplified by the radio frequency power amplifier 24 and is then passed to the ultrasonic transducer 12 by wires 13 and 14. The ultrasonic transducer 12 receives the electrical signal and transmits a corresponding ultrasonic signal, i.e., a tone burst in response.

The transmitted ultrasonic signal is reflected by tissue interfaces including moving interfaces in the blood stream, e.g., corpuscle-plasma interfaces. Echoes are sensed by the ultrasonic transducer which transmits an electrical signal to the transmitter-receiver in response to the received echoes. The received electrical signal contains information regarding the distance and velocity of tissues in the path of the sound signals. The interval between the transmission of electrical signals from the transmitter-receiver to the transducer is selected to allow the transducer to receive the ultrasonic echoes resulting from the tone burst and to transmit electrical signals to the transmitter-receiver in response to the received echoes before transmitting another tone burst.

The electrical signal received from the ultrasonic transducer is amplified by the radio frequency receiving amplifier 26 and is mixed by mixer 32 with the signal from the oscillator 21 to yield a signal comprising the sum and difference of the frequencies of the received signal and the oscillator signal.

The first delay function 31 and a second delay function 33 provide delayed gating signals for first and second sample and hold amplifiers 34 and 36 for sensing the velocity at two distances from the ultrasonic transducer as selected by first and second distance selectors 37 and 38, which are adjustable receiver gates. First and second band pass filters 39 and 41 eliminate those portions of the combined signals corresponding to the carrier signal, the sum of the combined signals and signals resulting from stationary interfaces, leaving only the portion of the combined signals resulting from motion of tissue interfaces at the two selected distances. The outputs of the band pass filters are then used to drive headphones or speakers 42 and 43 for providing audible signals. Alternatively, the outputs from the band pass filters can be used to produce analog voltages proportional to the respective velocities, which can be monitored and recorded, by using frequency to voltage converters.

By monitoring signals received from two different distances from the catheter tip, i.e., a first distance nearer the catheter tip and a second distance farther from the catheter tip, the blood velocity can be determined at those distances. These blood velocities are used to determine the presence and extent of a restriction in the blood vessel. A greater blood velocity, at the second distance as compared with that at the first distance, indicates a restriction in the blood flow at that second distance due to a narrowing of the blood vessel, e.g., due to the formation of tributaries, or as a result of the occlusion of the blood vessel by arteriosclerotic plaque. Conversely, a lower blood velocity at the second distance indicates greater patency of the blood vessel, possibly due to a broadening of the blood vessel or the absence of or at least a lesser amount of arteriosclerotic plaque at the second distance as compared with the first.

Figure 3:
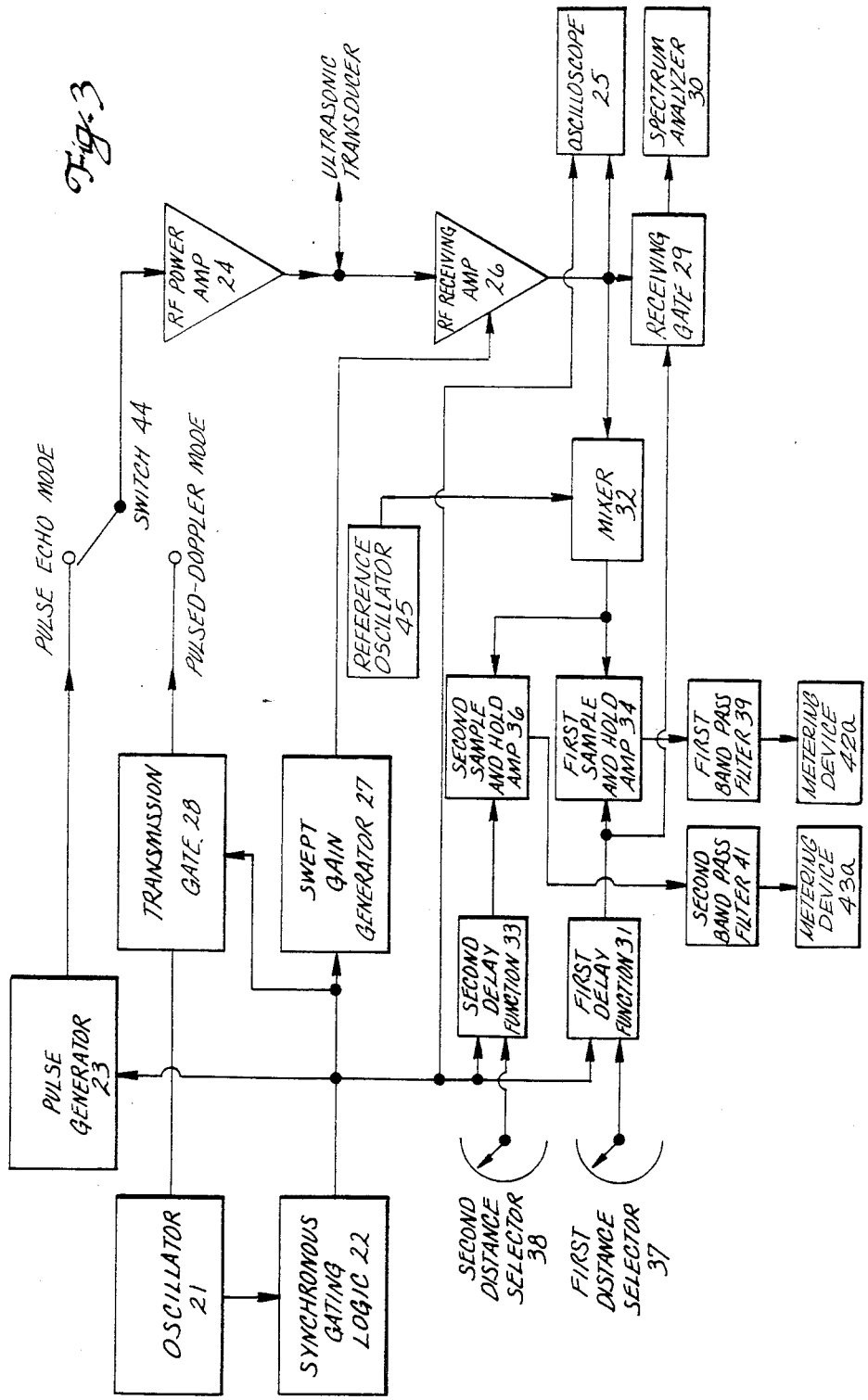
FIG. 3 is a block diagram of another transmitter-receiver applicable to the invention.

If desired, the direction of the blood flow can also be monitored. This can be accomplished by providing a reference frequency to the mixer 32 which is offset in frequency from oscillator 21. With reference to FIG. 3 the reference frequency can be generated, for example, by reference oscillator 45. In such an arrangement, the output signal can be monitored, for example, by metering devices 42a and 43a, each having an indicator. The indicator would be displaced in one direction from a zero position for motion toward the transducer and in the opposite direction for movement away from the transducer. The amount of displacement would indicate the velocity.

Figure 4:
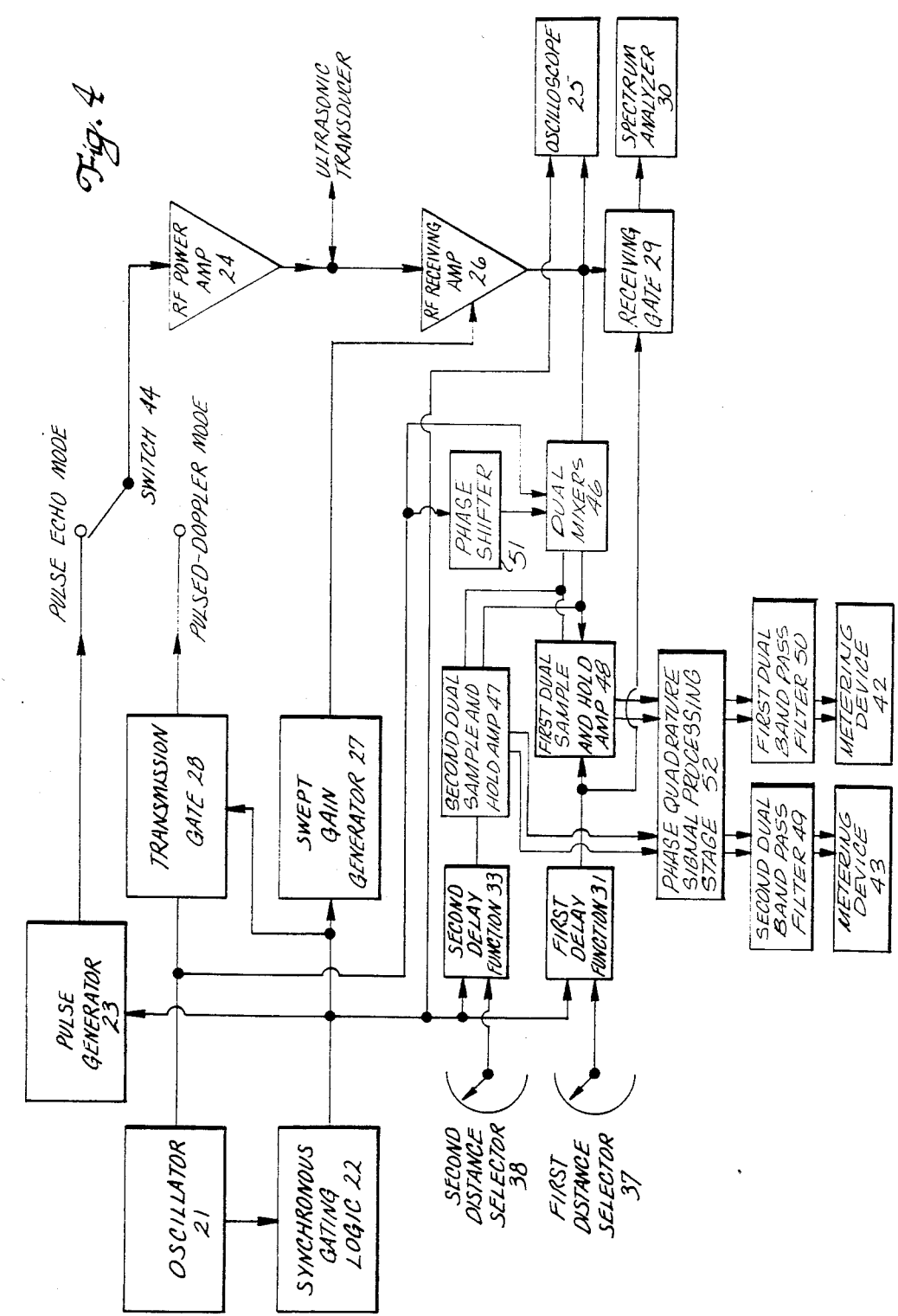
FIG. 4 is a block diagram of another transmitter-receiver applicable to the invention.

Alternatively, as shown in FIG. 4, by using dual channel circuitry from the mixer stage through the output stage, i.e., dual mixer 46, dual sample and hold amplifiers 47 and 48, and dual band pass filters 49 and 50, in conjunction with a phase shifter 51 and phase quadrature signal processing stage 52, direction sensing may also be provided, as is well known in the art.

The transmitter-receiver comprises a switch 44 for rapidly switching between the pulse-echo mode and the pulsed-doppler mode. Switching is sufficiently rapid that the received signals from both modes can be displayed "simultaneously". For example, the signals received in the pulse-echo mode can be displayed on an oscilloscope while the signals received in the pulsed-doppler mode can be used to drive a pair of speakers. Switching between modes is preferably sufficiently rapid so that, to an operator, each displayed signal appears continuous.

The combined information as to the position and extent of a blood vessel restriction and the character or properties of the restricting tissue provides an accurate determination of the presence, position and amount of restriction caused by arteriosclerotic plaque deposits and the need for its removal. Such removal can be effected immediately and with enhanced precision by vaporizing the plaque with laser irradiation delivered through the optical fiber.

Referring again to FIG. 1, the apparatus also comprises a laser 10 for generating the laser irradiation which is delivered through the optical fiber. Lasers for such applications are well known in the art. Suitable lasers include argon-ion, neodymium-YAG, and carbon dioxide lasers.

This invention provides several unique advantages over similar systems using a fiberoptic scope. For example, the presence of arteriosclerotic plaque deposits in a blood vessel can be determined without the need to stop the flow of blood through the blood vessel. Additionally, monitoring of the plaque deposits need not be interrupted by laser transmission. A catheter according to this invention can also be made sufficiently small to be positioned in coronary arteries and thus presents a new non-surgical treatment for heart disease due to occluded coronary arteries.

While the preceding description has been presented with reference to a presently preferred embodiment of the invention, it is apparent that changes and alterations in the above-described apparatus can be practiced without departing from the scope of the invention. For example, the ultrasonic transducer in the preferred embodiment described above is annular, i.e., disc-shaped and having a central opening. This enables the mounting of the distal tip of the optical fiber in the central opening. Further, the ultrasonic transducer is preferably mounted at a selected angle to the longitudinal axis of the catheter so that the transmitted ultrasonic signals are directed toward the wall of the blood vessels. However, other ultrasonic transducer shapes and mounting configurations are equally suitable as is mounting the distal tip of the optical fiber to one side of the ultrasonic transducer rather than through an opening in the transducer. Further, coupling optics are not required if it is desired to direct the laser irradiation in a direction generally along the length of the blood vessel rather than toward the blood vessel wall.

Figure 5:
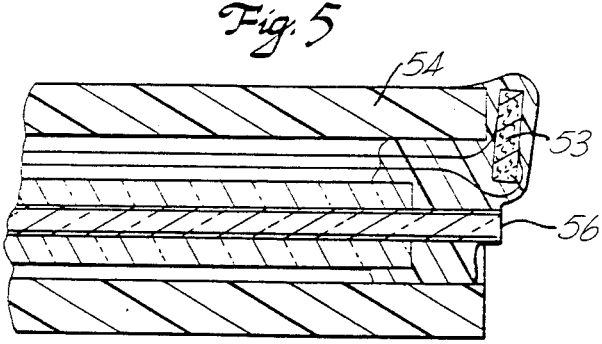
FIG. 5 is a cross-sectional view of another catheter according to the invention.

As illustrative, FIG. 5 shows rectangular ultrasonic transducer 53 mounted to the distal end of a catheter tube 54 with an optical fiber 56 extending through the catheter tube and mounted so that its distal end is to one side, e.g., below, the ultrasonic transducer. No coupling optics are used.

Figure 6:
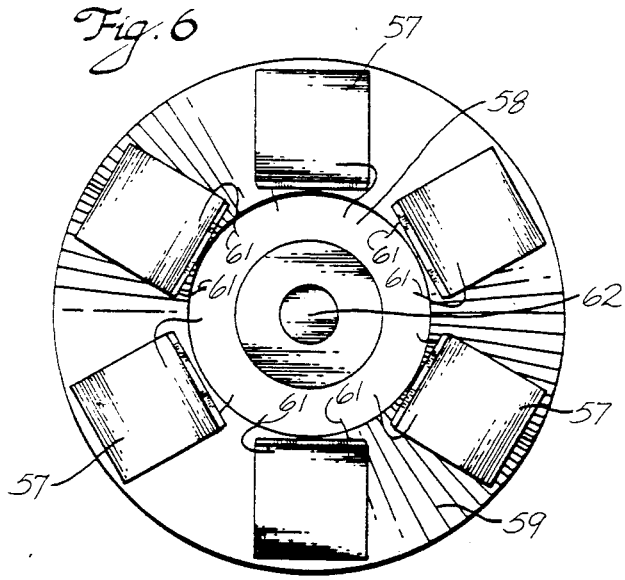
FIG. 6 is an end view of a catheter having a multielement ultrasonic transducer.

In another embodiment of the invention, the ultrasonic transducer may be comprised of a plurality of elements, each element being capable of independently transmitting and receiving ultrasonic signals. A preferred multiple-element ultrasonic transducer is shown in FIG. 6. The elements 57 are positioned symmetrically about the longitudinal axis of the catheter and provide a central opening 58 at the distal tip of the catheter. Each element 57 has a generally flat face and is mounted on the distal end of the catheter tube 59 at a select angle to the longitudinal axis of the catheter tube 59. Each element is electrically connected by separate pairs of wires 61 to the transmitter-receiver so that each element can be activated independently. An optical fiber 62 is disposed through the lumen of the catheter tube 59 and its distal tip is mounted in the central opening 58.

Multiple-element ultrasonic transducers provide the advantage that tissue signatures can be obtained in several radial directions without moving the catheter. However, for small blood vessels, e.g., coronary arteries, multiple-element ultrasonic transducers do not provide a significant advantage over single-element ultrasonic transducers and hence are not presently preferred.

Figure 7:
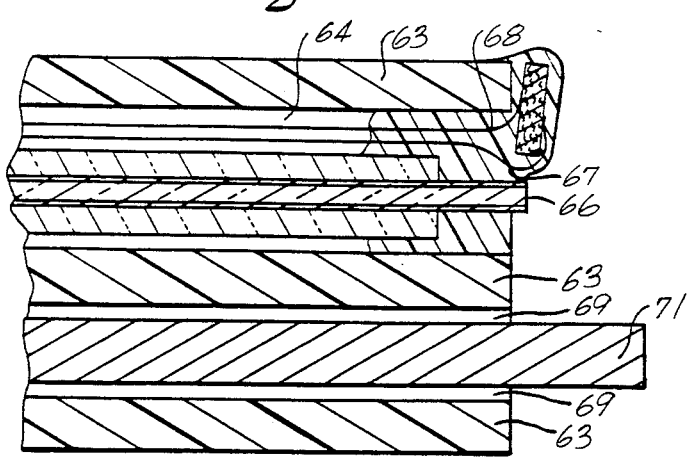
FIG. 7 is a cross-sectional view of a catheter having a second lumen for accommodating a guide wire.

If desired, the catheter tube can be designed to accommodate a guide wire to assist in the positioning of the catheter within the blood vessel. Such guide wires and their use are well known in the art. To accommodate a guide wire, the catheter tube can have a lumen sufficiently large to accommodate both the optical fiber and a guide wire and have an opening at the distal tip of the catheter to allow the distal extension of the guide wire. Alternatively, as shown in FIG. 7, the catheter tube 63 can comprise a first lumen 64 through which the optical fiber 66 and wires 67 and 68 are disposed and a second lumen 69 through which a guide wire 71 extends and is afforded lengthwise movement. Such a second lumen can also be used for the injection of a radiopaque fluid or other material into the blood vessel or the removal of fluid from the blood vessel.

What is claimed is:

1. A catheter adapted to be inserted into a blood vessel for identifying and removing arteriosclerotic plaque deposits in said blood vessel, said catheter having proximal and distal ends and a lumen comprising:
an elongated optical fiber having proximal and distal ends disposed within the lumen of the catheter tube and extending the length of the catheter tube for transmitting laser irradiation;
an ultrasonic transducer mounted at the distal end of the catheter adjacent the distal end of the optical fiber for transmitting the receiving ultrasonic signals; and
a pair of wires electrically connected to the ultrasonic transducer extending the length of the catheter.

2. A catheter as claimed in claim 1 wherein the ultrasonic transducer is a piezoelectric ceramic crystal.

3. A catheter as claimed in claim 1 wherein the ultrasonic transducer has a response frequency in the range of from about 10 to about 30 megahertz.

4. A catheter as claimed in claim 1 wherein the ultrasonic transducer is generally circular.

5. A catheter as claimed in claim 4 wherein the ultrasonic transducer comprises a circular opening through its center and wherein the distal tip of the optical fiber is mounted in the opening.

6. A catheter as claimed in claim 1 wherein the ultrasonic transducer is mounted at a selected angle of between 0° and 90° to the longitudinal axis of the catheter.

7. A catheter as claimed in claim 1 further comprising means for directing laser irradiation transmitted from the distal end of the optical fiber at a selected angle of from between 0° to 90° to the longitudinal axis of the catheter.

8. A catheter as claimed in claim 1 wherein the ultrasonic transducer comprises a plurality of elements, each element being capable of independently transmitting and receiving ultrasonic signals.

9. A catheter comprising:
an elongated, flexible catheter tube having proximal and distal ends and a lumen;
an elongated optical fiber having proximal and distal ends disposed within the lumen of the catheter tube and extending at least about the length of the catheter tube for transmitting laser irradiation;
an ultrasonic transducer having a generally flat face mounted to the distal end of the catheter tube at a selected angle to the longitudinal axis of the catheter tube; and
a pair of wires disposed within the lumen of the catheter tube and electrically connected to the transducer, said wires extending at least about the length of the catheter tube.

10. A catheter as claimed in claim 9 wherein the ultrasonic transducer is a piezoelectric ceramic crystal.

11. A catheter as claimed in claim 9 wherein the optical fiber is made of fused silica.

12. A catheter as claimed in claim 9 further comprising means for directing laser irradiation transmitted from the distal tip of the optical fiber at a selected angle from the longitudinal axis of the optical fiber.

13. A catheter as claimed in claim 12 wherein the means for directing laser irradiation transmitted from the distal end of the optical fiber at a selected angle to the longitudinal axis of the optical fiber comprises coupling optics mounted adjacent the distal end of the optical fiber so that laser irradiation emanating from the optical fiber passes through the coupling optics.

14. A catheter as claimed in claim 9 wherein the ultrasonic transducer comprises an opening through the ultrasonic transducer and wherein the distal end of the optical fiber is positioned in the opening.

15. A catheter as claimed in claim 9 wherein the diameter of the ultrasonic transducer is about 1 millimeter.

16. A catheter as claimed in claim 15 wherein the diameter of the optical fiber is from about 0.1 to about 0.5 millimeters.

17. A catheter as claimed in claim 9 wherein the lumen of the catheter tube is sufficiently large to provide a space extending the length of the catheter tube between the optical fiber and the wall of the catheter tube and wherein the catheter tube comprises at least one hole through the wall of the catheter tube near the distal end of the catheter tube.

18. A catheter as claimed in claim 9 wherein the catheter tube comprises a second lumen which is open at the distal tip of the catheter.

19. A catheter as claimed in claim 18 further comprising a guide wire disposed in the second lumen and afforded lengthwise movement through the second lumen.

20. An apparatus comprising:
a catheter adapted to be inserted into a blood vessel for identifying and removing arteriosclerotic plaque deposits in said blood vessel, said catheter having proximal and distal ends a lumen comprising:
an elongated optical fiber having proximal and distal ends disposed within the lumen of the catheter and extending the length of the catheter lumen for transmitting from its distal end laser irradiation which has been applied to its proximal end;
an ultrasonic transducer at the distal end of the catheter adjacent the distal end of the optical fiber for transmitting and receiving ultrasonic signals;
a pair of wires having proximal and distal ends and expanding the length of the catheter electrically connected at their distal ends to the ultrasonic transducer;
a transmitting unit electrically connected to the proximal ends of the wires for generating electrical impulses for activating the ultrasonic transducer to transmit ultrasonic signals; and
a receiving unit electrically connected to the proximal ends of the wires for receiving and displaying electrical signals transmitted by the ultrasonic transducer in response to ultrasonic signals received by the ultrasonic transducer.

21. An apparatus as claimed in claim 20 wherein the transmitting unit comprises:
a pulse-echo mode for generating short electrical impulses for activating the ultrasonic transducer to transmit ultrasonic pulse signals;
a pulsed-doppler mode for generating electrical bursts for activating the ultrasonic transducer to transmit ultrasonic tone bursts; and
means for switching between the pulse-echo mode and the pulsed-doppler mode.

22. An apparatus as claimed in claim 20 wherein the receiver comprises an oscilloscope for displaying electrical signals received from the ultrasonic transducer.

23. An apparatus as claimed in claim 20 wherein the receiver comprises speakers for audibly monitoring electrical signals received from the ultrasonic transducer.

24. An apparatus as claimed in claim 20 further comprising a laser for applying laser irradiation to the proximal end of the optical fiber.

25. A method for removing occlusions in blood vessels comprising the steps of:
(a) inserting into a blood vessel a catheter comprising:
(1) an optical fiber for transmitting laser irradiation;
(2) an ultrasonic transducer at the distal tip of the catheter for transmitting and receiving ultrasonic signals;
(b) activating the ultrasonic transducer to transmit short ultrasonic pulse signals at selected intervals;
(c) receiving ultrasonic echoes resulting from the transmitted ultrasonic pulse signals;
(d) determining the presence and character of occlusions in the blood vessel based upon the received ultrasonic echoes; and
(e) directing sufficient laser irradiation through the optical fiber onto occlusions whose presence and character have been determined to remove at least a portion of the occlusion.

26. A method as claimed in claim 25 further comprising, prior to step (d) of claim 25:
(a) activating the ultrasonic transducer to transmit tone bursts at selected intervals;
(b) receiving ultrasonic echoes resulting from the transmitted tone bursts;
(c) determining the velocity of blood flow at two selected distances from the catheter tip from the received ultrasonic echoes of the tone burst; and
(d) determining the presence and character of occlusions based upon the ultrasonic echoes received in response to transmitted ultrasonic pulse signals and upon the velocity of blood flow at two selected distances from the catheter tip.

27. A method as claimed in claim 25 further comprising, prior to step (d), determining the direction of the blood flow at the two selected distances from the catheter tip from the received ultrasonic echoes of the toneburst.

* * * * *